(12) United States Patent
Sun et al.

(10) Patent No.: US 9,090,578 B2
(45) Date of Patent: Jul. 28, 2015

(54) PREPARATION METHOD OF GLYCIDYL TERTIARY CARBONIC ESTER

(71) Applicant: Tianjin Shield Specialty Chemicals Co., Ltd., Tianjin (CN)

(72) Inventors: Lanbo Sun, Tianjin (CN); Tao Yang, Tainjin (CN); Honghai Li, Tianjin (CN); Yingchun Lou, Tianjin (CN)

(73) Assignee: Tianjin Shield Specialty Chemicals Co., Ltd., Tianjin (CN)

( * ) Notice: Subject to any disclaimer, the term of this patent is extended or adjusted under 35 U.S.C. 154(b) by 0 days.

(21) Appl. No.: 14/369,519

(22) PCT Filed: Dec. 26, 2012

(86) PCT No.: PCT/CN2012/087553
§ 371 (c)(1),
(2) Date: Jun. 27, 2014

(87) PCT Pub. No.: WO2013/097724
PCT Pub. Date: Jul. 4, 2013

(65) Prior Publication Data
US 2014/0364635 A1  Dec. 11, 2014

(30) Foreign Application Priority Data
Dec. 28, 2011 (CN) .......................... 2011 1 0447712

(51) Int. Cl.
*C07D 301/24* (2006.01)
*C07D 301/26* (2006.01)
*C07D 303/16* (2006.01)
*C07C 67/00* (2006.01)
*C07C 67/26* (2006.01)

(52) U.S. Cl.
CPC .............. *C07D 301/26* (2013.01); *C07C 67/00* (2013.01); *C07C 67/26* (2013.01); *C07D 303/16* (2013.01)

(58) Field of Classification Search
CPC .... C07D 303/16; C07D 301/26; C07C 67/00; C07C 67/26
USPC ........................................... 549/520
See application file for complete search history.

(56) References Cited

U.S. PATENT DOCUMENTS 6,433,217 B1 *  8/2002  Rosenbrand et al. ......... 560/263

FOREIGN PATENT DOCUMENTS

| CN | 101245053 B | 4/2011 |
| WO | WO 97/44335 | 11/1997 |
| WO | WO 00/17179 | 8/2000 |

* cited by examiner

*Primary Examiner* — T. Victor Oh
(74) *Attorney, Agent, or Firm* — Brinks Gilson & Lione

(57) ABSTRACT

The present disclosure provides a preparation method of glycidylester of tertiary carbonic acid. The synthesis is performed in two steps: first, the tertiary carbonic acid reacts with a halo substituted epoxide under a catalyst to produce tertiary carbonic halo substituted alcohol ester; after dehydrohalogenation of the halo substituted alcohol ester of tertiary carbonic acid, the glycidylester of tertiary carbonic acid is formed. In the first step of preparing the halo substituted alcohol ester of tertiary carbonic acid through synthesis, the reaction between the tertiary carbonic acid and the halo substituted epoxide is only performed in the existence of water and the catalyst, and the water comprises water added before the reaction. The present disclosure significantly increases the product output in the unit volume, and is particularly suitable for industrial production of glycidylester of tertiary carbonic acid having the low cost, high purity, low color and stable color.

16 Claims, No Drawings

PREPARATION METHOD OF GLYCIDYL TERTIARY CARBONIC ESTER

This application is the national phase application of PCT Application No. PCT/CN2012/087553 filed Dec. 26, 2012, which claims priority to Chinese Patent Application No. 201110447712.4 filed Dec. 28, 2011, the entireties of both of which are incorporated herein by reference.

TECHNICAL FIELD

The present disclosure relates to the field of organic compound synthesis, more particularly a method for synthesis of glycidylester of tertiary carbonic acid.

BACKGROUND

Glycidyl tertiary carbonic ester is a highly branched glycidyl ester of α-branch monosaturated aliphatic acid (also referred to as glycidyl ester of branched carboxylic acid). The product can be used to prepare acrylic acid modified resins, polyester modified resins, alcohol acid modified resins and epoxy resins. It can also be used as active diluents for paints. It can significantly improve the properties of paints and is an important raw material for high-quality car paints, coil paints and metal paints.

Among the present technologies, the preparation of glycidylester of tertiary carbonic acid by the reaction between tertiary carbonic acid and halo substituted monoepoxides is mainly achieved by a two-step method, i.e. the first step is synthesis of intermediate product of halo substituted alcohol ester of tertiary carbonic acid, and the second step is conversion from the intermediate product into the final product glycidylester of tertiary carbonic acid.

For example, the glycidylester of tertiary carbonic acid could be directly prepared with carbonic acid and epoxy chloropropane, under catalysis of alkali metal hydroxide as well as dehydrochlorination, wherein glycidyl ester, alkali metal salt and water are produced. During this process, several high boiling point byproducts can be produced, with different yields, which may comprise halo substituted alcohol ester derivatives, derivatives produced by the reaction of halo substituted alcohol ester and epoxy chloropropane, and derivatives of glycidyl ester, presenting about 8%-12% of the total weight of the product. As the glycidylester of tertiary carbonic acid is easily deteriorated under heat or acidic or basic condition, therefore, the heating time for its purification by distillation is strictly limited. WO 97/44335 disclosed a method by which a product with a purity of 99% could be obtained. The product has a light color, and the color is stable during storage, but the product yield is relative low, 30% only, thus the cost is relatively high, and the industrial productive value is relatively low.

A method for the preparation of glycidyl esters of branched monocarboxylic acids was published in Chinese Patent CN99811327.1, wherein in the presence of water and a water-miscible solvent (isopropanol), catalyzed with catalyst (alkali metal hydroxide or alkali metal alkoxide), carboxylic acid reacts with halo substituted epoxides. Then by the dehydrohalogenation via the addition of base in two steps, glycidyl ester, alkali metal salt and water were produced. According to CN99811327.1, color-stable, during storage, glycidyl ester of branched monocarboxylic acids with very high level purity were obtained without distillation, and the content of high boiling point byproducts was lower than 6 wt %.

However, this method presents the following defects:

1. Water-miscible solvent is applied in the first step of catalytic synthesis. Large amount of water was required in this step (total amount of water is 4-13 times of the mole of carbonic acid). Due to the low concentration of saline water produced, it is unavoidable to bring some of the solvent, halo substituted epoxy propane and the product obtained into the diluted saline water while separating the saline water obtained during the first step, resulting in the loss of the solvent, halo substituted epoxy propane and the product. As for the recovery of organics in said diluted saline water, in one hand, raw materials and products would be lost due to incomplete recovery of solvent and thus poor recovery of halo substituted epoxy propane and products produced; in another hand, unrecovered halo substituted epoxy propane and products produced would become waste water or solid waste and then affect the environment.

2. Example 1 of CN99811327.1 shows that, large amount of isopropanol was used in the first step of catalytic synthesis, about 35% of the total reaction volume, which causes significant decrease of yield per unit volume. Therefore, this method is not suitable for industrial production. Meanwhile, side reactions between isopropanol and halo substituted epoxy propane will result undesired lost for halo substituted epoxy propane preparation.

3. Side reactions may occur during the first dehydrohalogenation by the addition of base because of the presence of halo substituted epoxy propane, resulting in the unnecessary loss of the halo substituted epoxy propane, thus reduced recovery rate of the raw material is decreased, which also causes increase of high boiling point byproducts, and the quality of the product is decreased.

4. The amount of epoxy chloropropane in the reaction was about 23% of the total reaction volume during the first dehydrohalogenation, which causes significant decrease of yield per unit volume. Therefore, this method is not suitable for industrial production.

5. While recovering halo substituted epoxy propane and solvent that is miscible with water by distillation, not only the recovery rate of the solvent and the halo substituted epoxy propane is reduced in the method because of the above reasons but also the solvent obtained is a mixed solvent, which is not suitable to be reused.

6. Second dehydrohalogenation is required for the method because the first dehydrohalogenation is not complete. The hydrolysis of the glycidyl ester is not avoidable during the second dehydrohalogenation. Thus the purity of the product is decreased, additional preparation procedures are required, and the preparation time is prolonged, so it is not suitable for industrial production.

In addition, a two-step synthesis method for glycidylester of tertiary carbonic acid was disclosed in Chinese patent CN200710056829.3. At first, the halo substituted alcohol ester of tertiary carbonic acid is produced by the reaction of carbonic acid and halo substituted epoxy propane under the catalysis of organic quaternary ammonium salt. Then glycidylester of tertiary carbonic acid, alkali metal salt and water are produced by the dehydrohalogenation via the addition of alkali metal hydroxide. Quaternary ammonium salt is used as a catalyst in this method, which also has some defects: at first, alkali metal hydroxides and alkali metal salts which are not solvable in the organic phase were brought into the organic phase by forming ion pair with tetra-alkyl ammonium ion via quaternary ammonium salt under action of lipophilic ammonium ion, resulting in the emulsification of the glycidyl ester; secondly, the organics can be brought into the aqueous phase by the charge effect of the lipophilic ammonium ion, causing the increase of the COD value of the waste water, thus resulted in more serious environmental pollution and loss of product. In order to solve the problems, the glycidylester of tertiary carbonic acid obtained by synthesis has to be separated and purified by distillation In this process, due to the heat-lability property of glycidylester of tertiary carbonic acid, decrease of the synthesis yield is unavoidable.

In conclusion, the method for preparing glycidylester of tertiary carbonic acid needs to be improved continuously, to improve the quality of the products, to decrease the cost and the influence to the environment and to be more suitable for industrial production.

SUMMARY

The present disclosure is aim to provide a simpler and more effective method to significantly increase the product yield per unit volume.

The present disclosure is also aimed to provide a process for producing glycidylester of tertiary carbonic acid which is more suitable for industrial production with low cost, high purity, light and stable color. The present disclosure also aims to provide an improved technical solution for industrial production which can significantly decrease the consumption of raw materials (mainly the consumption of halo substituted epoxy propane), decrease the production of high boiling point byproducts, decrease the discharge of substances of environment harmful, and decrease steps of production.

In order to achieve the mentioned purposes, the present disclosure provides a preparation method for glycidylester of tertiary carbonic acid.

A two-step synthesis of glycidylester of tertiary carbonic acid is adopted to obtain glycidylester of tertiary carbonic acid having 5-20 carbon atoms, preferably 9-13 carbon atoms, which comprises:

The first step, the preparation of halo substituted alcohol ester of tertiary carbonic acid: in the presence of water and catalyst only, the tertiary carbonic acid reacts with halo substituted epoxides to form halo substituted alcohol ester of tertiary carbonic acid; wherein said water includes pre-added water for the reaction; wherein the catalyst is preferably a basic catalyst.

More preferably, the excess (unreacted) halo substituted epoxide is removed when the reaction is finished.

The second step, the preparation of glycidylester of tertiary carbonic acid: a water-miscible solvent is added to dissolve the product obtained in the first step; alkali metal hydroxides or alkali metal alkoxides are added to obtain glycidylester of tertiary carbonic acid. The preferable solvent is low chain aliphatic alcohols, and solvent with low boiling point is more preferable.

The preparation equation is shown as below:

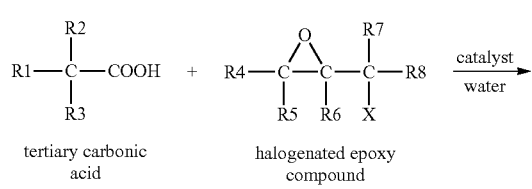

(1)

tertiary carbonic acid + halogenated epoxy compound

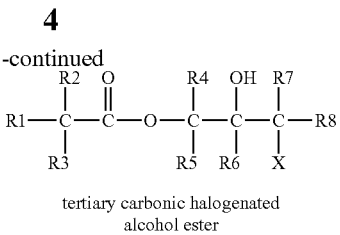

tertiary carbonic halogenated alcohol ester (2)

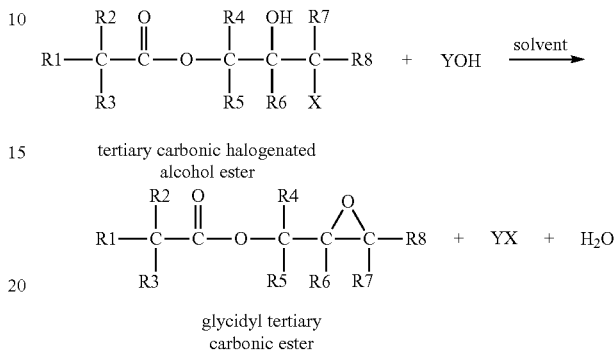

tertiary carbonic halogenated alcohol ester glycidyl tertiary carbonic ester

Wherein R1, R2 and R3 represent alkyl substituents, at least one of which is methyl, the rest of which are linear or branch chain alkyls, the total number of carbon atoms being 3-18; R4-R8 represent hydrogen or alkyls. For example, when the total number of carbon atoms of R1, R2, R3 is 8, and R4-R8 are hydrogen, the glycidylester of tertiary carbonic acid produced is glycidylester of neodecanoic acid by the reaction of neodecanoic acid and epoxy chloride propane. The X in the equation represents halogen, such as chlorine, bromine, iodine; Y represents alkali metal, such as sodium, potassium.

Simpler and better is the beauty of science. It is found in the present disclosure upon creative imagination and repeated scientific experiments that:

In the first step of synthesis of glycidylester of tertiary carbonic acid: during the synthesis of halo substituted alcohol ester of tertiary carbonic acid by the reaction of tertiary carbonic acid and halo substituted epoxide in the presence of water and catalyst only, halo substituted alcohol ester of tertiary carbonic acid and a small amount of glycidylester of tertiary carbonic acid can be obtained. The total amount of water is 2-14 times of the mole of tertiary carbonic acid, preferably 3.5-10 times, more preferably 3.7-5 times. The total amount of water includes water added in advance, water contained within the catalyst and water produced during the reaction. The pre-added water mainly acts as a dispersant, which is advantageous for stabilizing the reaction.

The experiment data of the reaction show that the intermediate product, halo substituted alcohol ester of tertiary carbonic acid, can be synthesized with a very high yield rate by tertiary carbonic acid and halo substituted epoxide under the action of catalyst with only dispersant of water. In addition, halo substituted alcohol ester of tertiary carbonic acid is an intermediate product that is relatively stable. Therefore, it can be produced and separated, and then be used to synthesize glycidylester of tertiary carbonic acid.

We also found that in the second step of the reaction, i.e., the process of producing glycidylester of tertiary carbonic acid by the dehydrohalogenation of the intermediate product, halo substituted alcohol ester of tertiary carbonic acid, with bases, the presented halo substituted epoxide did not provide any action except causing side reactions and producing impurities. Therefore, before carrying out the second step of the reaction, it is necessary to remove unreacted halo substituted epoxide to recover halo substituted epoxide maximally for reuse, thus lowering the cost.

In addition, in the second step of the method, alkali metal hydroxides or alkali metal alkoxides are used for the dehydrohalogenation of the intermediate product, halo substituted alcohol ester of tertiary carbonic acid, (in the first step and the second step of the reaction, preferably excess amount of basic compound is added to completely remove halogen hydride), then to prepare glycidylester of tertiary carbonic acid; the residual of alkali metal hydroxide or alkali metal alkoxide is removed, then the low boiling point solvent is removed by distillation to obtain glycidylester of tertiary carbonic acid with high purity. Compared with the techniques in the art, twice dehydrohalogenation is not required in the method of the present disclosure.

On the basis of the technical solution, the preparation process of the present disclosure further comprises:

In the first step, after the synthesis reaction of tertiary carbonic acid and halo substituted epoxide, the product is stood to stratify, thus the lower saline water is separated; the unreacted halo substituted epoxide is removed or removed and recovered. The recovered halo substituted epoxide can be reused.

During said step, the removal of unreacted halo substituted epoxide is achieved, preferably but not limited to, by vacuum distillation.

In the first step, the catalyst can be one of the following basic catalysts: alkali metal hydroxides, alkali metal carbonates, alkali metal hydrocarbonates or alkali metal alkoxides, preferably sodium hydroxide or potassium hydroxide, wherein the concentration of sodium hydroxides is 30-50 wt %, preferably 40-50 wt %. In the reaction, the maximum amount of a basic catalyst added is 40 mol % of the mole of tertiary carbonic acid, preferably 20-30 mol %, more preferably 20 mol %.

In the first step, the halo substituted epoxide is epoxy halo propane, preferably epoxy chloropropane.

In the first step, the amount of added tertiary carbonic acid to halo substituted epoxide is 1:1.5-20 in molar ratio, preferably 1:1.8-20.

In the first step, the reaction is carried out at 30° C.-110° C. with rapid stirring for 0.5 h -2.5 h.

In the second step, the specific steps are: water-miscible solvent is added to dissolve the production obtained in the first step, and additional alkali metal hydroxides or alkali metal alkoxides are added to react; the reaction mixture is allowed to stratify after the reaction, and the lower saline water is separated; adjusting the obtained upper organic phase to neutral by adding acidifier or by passing through $CO_2$, small amount salt produced is removed. The molar ratio of the amount of added alkali metal hydroxide or alkali metal alkoxide to the tertiary carbonic acid of the first step is 0.9-1.1:1, preferably 1:1.

Preferably, the second step further comprises: the organic phase neutralized is removed by distillation, and the solvent is recovered; the product obtained after removing the solvent is washed with water to obtain the product, halo substituted alcohol ester of tertiary carbonic acid, by distillation or dehydration with desiccant.

In the second step, the reaction is completed at 20° C.-80° C. with rapid stirring.

In the second step, the acidifier is a diluted strong acid or an acidic salt. The diluted strong acid can be selected from the group consisting of diluted sulphuric acid and diluted hydrochloric acid. The acidic salt is preferably sodium dihydrogen phosphate.

In the second step, the alkali metal hydroxide is preferably sodium hydroxide, the alkali metal alkoxide is preferably sodium alkoxide of 1-6 carbon atoms, wherein the concentration of sodium hydroxide is 15 wt %-40 wt %, preferably 20 wt %-30 wt %.

In the second step, the solvent is low carbon chain aliphatic alcohols, such as methanol, ethanol, propanol, isopropanol, butanol, tertiary butanol, preferably isopropanol. The molar ratio of the amount of the added solvent to the tertiary carbonic acid of the first step is 1-6:1, preferably 1-4:1.

According to one of the preferred embodiment of the present disclosure, the method comprises the following steps:

(1) The preparation of halo substituted alcohol ester of tertiary carbonic acid React tertiary carbonic acid with halo substituted epoxide with the molar ratio of the tertiary carbonic acid to the halo substituted epoxide being 1:1.5-20, in the presence of water and in the presence of basic catalyst with the maximum amount of 30 mol % of the mole of tertiary carbonic acid and under rapid stirring at 30-110° C. for 0.5 h-2.5 h; the reaction mixture is allowed to stratify and then the lower saline water is separated; unreacted halo substituted epoxide is removed and recovered by reduced pressure distillation to obtain halo substituted alcohol ester of tertiary carbonic acid and a small amount of glycidylester of tertiary carbonic acid;

(2) The preparation of glycidylester of tertiary carbonic acid

All the products obtained from step (1) are dissolved in water-miscible isopropanol; under 20° C.-80° C., preferably 40° C.-60° C. with rapid stirring, alkali metal hydroxide(s) or alkali metal alkoxide(s) with the amount of mole equal to tertiary carbonic acid of step (1) are added to react; the reaction mixture is allowed to stratify after reaction, and the lower saline water is separated; then adjust the obtained upper organic phase to neutral by adding acidifier or by passing through $CO_2$, then remove the salt produced; remove the organic phase by distillation, recover the aliphatic alcohol; then wash the obtained product with water to remove the salt remained, obtain the glycidylester of tertiary carbonic acid produced by distillation or dehydration via desiccant.

The method of the present disclosure can be carried out with batch operation or continuous operation.

In the step (1), the molar ratio of tertiary carbonic acid to epoxy chloropropane is preferably 1:1.8-20.

In the step (1), the total amount of water is 2-10 times of the mole of tertiary carbonic acid, preferably 3.5-10 times.

In the step (1), the reaction is preferably carried out at 50° C.-95° C. with rapid stirring of 1 h-2 h, more preferably 1 h-1.5 h.

In the step (2), adding all the products obtained from step (1) to the isopropanol with the mole equals to 1-4 times of the mole of tertiary carbonic acid for dissolution; preferably 2-3 times.

In the step (2), the reaction is carried out at 50° C.-60° C.

The term "rapid stirring" in steps (1)-(2) means to allow sufficient contact between the aqueous phase and the organic phase.

The term "distillation" in steps (1)-(2) means to remove the low boiling point head fraction from the reaction mixture initially obtained.

The tertiary carbonic acid used as raw material in the present disclosure is the tertiary carbonic acid with 5-20 carbon atoms, preferably tertiary carbonic acid with 5-13 carbon atoms, most preferably tertiary carbonic acid with 9-11 carbon atoms.

The advantages of the present disclosure lie in: the method of the present disclosure only comprises two steps. In the first step, only water is used as solvent, and in the second step, glycidylester of tertiary carbonic acid with high purity can be obtained without halo substituted epoxide. The content of high boiling point byproducts in the final product can reach to lower than 6 wt %, or even lower than 4 wt %; meanwhile, the initial color of the final product is light and stable during storing, and distillation is not required to remove the high boiling point byproducts for purification.

Besides, the method provides more advantages such as:

1. Water, rather than water-miscible solvents, is used as dispersant during synthesis of halo substituted alcohol ester of tertiary carbonic acid in the first step. The difficulty of recovering the halo substituted epoxy propane and halo substituted alcohol ester of tertiary carbonic acid contained in the discharged diluted saline water which is separated after reaction, caused by the addition of water-miscible solvents, is solved. The method of the present disclosure significantly improves the yield of production, lowering the consumption of raw material and decreasing the discharge of the substance that is harmful to the environment.

2. After the synthesis of halo substituted alcohol ester of tertiary carbonic acid, the recovery of the excess and unreacted halo substituted epoxide in the product with high yield can be achieved industrially because the boiling point of the intermediate product is relative high, and no other solvent is presented, therefore, the consumption of the raw material is lowered.

3. The amount of byproducts produced is decreased in the second step of synthesis of glycidylester of tertiary carbonic acid by carbonic halo substituted alcohol ester as no halo substituted epoxide is presented, the quality of the product is increased and unnecessary consumption of the halo substituted epoxide is avoided.

4. The time required for the preparation is shortened because the second dehydrohalogenation by the addition of alkali metal hydroxide after obtaining the glycidylester of tertiary carbonic acid is not required and thus diminishing one preparation step; meanwhile, the decrease of yield by the damage to the produced glycidylester of tertiary carbonic acid by base is avoided, so does the generation of the byproducts that are harmful to the quality of the product.

5. The product output per unit volume is significantly increased as no solvent is used in the first step and no halo substituted epoxide is used in the second step, the cost of manufacturing devices is saved, thus it is more suitable for industrial production.

DETAILED DESCRIPTION OF THE PREFERRED EMBODIMENTS

The embodiments below are used to illustrate the present disclosure. However, the extent of the present disclosure is not limited thereto. It can be understood by those skilled in the art that parameters such as reaction temperature, time, amount of addition of raw materials, concentration of raw materials mentioned in the examples below can be adjusted within their effective extent, the reaction processes and the final product obtained in the reactions will be the same. Although it is not provided in the examples below, the other basic catalysts mentioned in the present disclosure such as alkali metal carbonates, alkali metal alkoxides share the same reaction mechanism and property in the reaction of the present disclosure for those skilled in the art. For example, alkoxides with 1-6 carbon atoms are solvable in the reaction medium, and can produce hydroxyl anion, which are similar to the hydroxyl anions produced by sodium hydroxides, and the property of the product will be the same.

Example 1

(1) The preparation of tertiary carbonic chlorinated alcohol ester

The initial reaction materials were added to a 1 L reactor equipped with a mechanical stirrer, a water-bath heater and a reflux unit.

| (1) The preparation of tertiary carbonic chlorinated alcohol ester | | | | |
|---|---|---|---|---|
| | Weight (g) | Volume (mL) | Moles | Molar ratio |
| Initial reaction material | | | | |
| SHINA-10 acid | 226.00 | 248.35 | 1.31 | 1.00 |
| Epoxy chloropropane | 485.53 | 411.47 | 5.25 | 3.99 |
| Water | 94.60 | 94.60 | 5.26 | 4 |
| Total amount | 806.13 | 754.42 | | |
| The addition of catalyst | | | | |
| 40% sodium hydroxide | 27.05 | 18.92 | 0.27 | 0.21 |
| Total reaction volume | | 773.34 | | |

The SHINA-10 acid in the above mentioned table and further mentioned below is neodecanoic acid and it is commercially available, wherein, SHINA is the trademark of HEBEI SIYOU ZHUO YUE SCIENCE & TECHNOLOGY LIMITED.

It should be noted that the "water" in said example and the examples below is the water added before the beginning of the first step reaction.

Stirring was initialized, under rapid stirring, the initial reaction material was heated to 50° C.-55° C., and then the aqueous solution of sodium hydroxide (40 wt %) was added within 20 min-25 min, with 27.05 g of the aqueous solution added in total.

In the present example, the molar ratio of tertiary carbonic acid to the total amount of water was 1:4.91, wherein, the molar ratio of tertiary carbonic acid:water added: water brought by sodium hydroxide:water produced in acid base reaction=1:4:0.7:0.21.

The temperature was raised up to 84° C.-86° C. within 20 minutes then maintained at this temperature for 40 minutes. Then the temperature of the reaction mixture was rapidly dropped to 60° C.-70° C. Stirring was stopped, stood for 5-10 minutes to allow the two phases of the reaction mixture stratified sufficiently, 94.76 g of lower saline water was discharged. The upper organic phase was distilled with reduced pressure with rotating film evaporator in oil-bath under 100° C., 353.6 g of epoxy chloropropane was removed, and 342 g of tertiary carbonic chlorinated alcohol ester with small amount of glycidylester of tertiary carbonic acid were obtained.

(2) The preparation of glycidylester of tertiary carbonic acid

All the mixture of tertiary carbonic chlorinated alcohol ester and glycidylester of tertiary carbonic acid were added to the 1 L reactor equipped with a mechanical stirrer, a water-bath heater and a reflux unit, and then 236.79 g of isopropanol was added.

(2) The synthesis of glycidylester of tertiary carbonic acid

|  | Weight (g) | Volume (mL) | Moles | Molar ratio |
|---|---|---|---|---|
| Initial reaction material | | | | |
| Products of (1) | 342 | | | |
| Isopropanol | 236.79 | 301.6 | 3.94 | 3.00 |
| Sum | | 648.51 | | |
| The addition of sodium hydroxide | | | | |
| First 24% of sodium hydroxide | 108.97 | 86.14 | 0.65 | 0.50 |
| Second 24% of sodium hydroxide | 108.97 | 86.14 | 0.65 | 0.50 |
| Total volume | | 734.65 | | |

Stirring was initialized, under rapid stirring, the temperature of the initial reaction material was maintained at 50° C.-55° C., and then 108.97 g of the aqueous solution of sodium hydroxide (24 wt %) was added within 10 min-15 min, the temperature was maintained for 30 minutes, then waited still for 5 minutes for the reaction mixture to sufficiently separate into a upper layer and a lower layer, 82.94 g of the lower saline water was discharged.

Stirring was initialized again, under rapid stirring, the upper layer organic phase was obtained by separation and the temperature thereof was maintained at 50° C.-55° C., and then 108.97 g of the aqueous solution of sodium hydroxide (24 wt %) was added within 10 min-15 min, the temperature was maintained for 30 minutes, then waited still for 10 minutes for the reaction mixture to sufficiently separate into a upper layer and a lower layer, 141.93 g of the saline water was discharged.

Stirring was initialized again, under rapid stirring, the upper layer organic phase was obtained by separation and the temperature thereof was maintained at 50° C.-55° C., $CO_2$ gas was passed through to adjust the organic phase to pH=7-9, small amount of salt precipitate appeared. The insoluble substances were removed by filtration.

The obtained clear organic phase was distilled under reduced pressure with rotatory film evaporator. 227.5 g of isopropanol was removed.

100 g of water was added to the organic phase remained, stirred for 10 minutes at 50° C.-55° C., waited still for 10 minutes, then 85.68 g of aqueous phase of the layer below was discharged.

Then 301 g of the obtained upper organic phase was distilled under reduced pressure, 45 mmHg, 90° C.-100° C., dehydration and dried.

288 g of glycidyl ester of SHIVA-10 acid with high purity was finally obtained.

The quality of the glycidylester of tertiary carbonic acid is as follows:

Epoxy value (EGC): 4212

Purity: 96.18%

Hydrolysable chloride: 322 mg/kg

Color: 15 (Pt/Co)

The production index of the method is as follows:

Yield: 96.2% (based on the amount of the SHIVA-10 acid fed)

Recovery rate of epoxy chloropropane: 97.2%

Recovery rate of isopropanol: 96.1%

Example 2

The procedure of example 1 was repeated with different amount of raw materials added, see table below for details.

In this example, the molar ratio of tertiary carbonic acid to the total amount of water was 1:3.24, wherein, the molar ratio of tertiary carbonic acid:water added: water brought by sodium hydroxide:water produced in acid base reaction=1: 2.33:0.7:0.21.

|  | Weight (g) | Volume (mL) | Moles | Molar ratio |
|---|---|---|---|---|
| The preparation of tertiary carbonic chlorinated ester | | | | |
| Initial reaction material | | | | |
| SHINA-10 acid | 226.00 | 248.35 | 1.31 | 1.00 |
| Epoxy chloropropane | 182.31 | 154.50 | 1.97 | 1.50 |
| Water | 55.00 | 55.00 | 3.06 | 2.33 |
| Sum | 463.31 | 457.85 | | |
| The addition of catalyst | | | | |
| 40% of sodium hydroxide | 27.05 | 18.92 | 0.27 | 0.21 |
| The total reaction volume | | 476.77 | | |
| The synthesis of glycidylester of tertiary carbonic acid | | | | |
| Initial reaction material | | | | |
| Intermediate product | | | | |
| Isopropanol | 157.94 | 202.48 | 2.63 | 2.00 |
| Sum | | 202.48 | | |
| The addition of sodium hydroxide | | | | |
| First 24% sodium hydroxide | 108.97 | 86.14 | 0.65 | 0.50 |
| Second 24% sodium hydroxide | 108.97 | 86.14 | 0.65 | 0.50 |

|  | Example 2 |
|---|---|
| Quality Index | |
| Epoxy Value (EGC) | 4106 |
| Purity % | 93.77 |
| Hydrolysable chloride mg/kg | 641 |
| Color: (Pt/Co) | 20 |
| Production Index | |
| Recovery rate of epoxy chloropropane % | 96.7 |
| Recovery rate of isopropanol % | 95 |

The procedure of example 1 was repeated in the following examples 3-6 with the molar ratio of tertiary carbonic acid to epoxy chloropropane=1:2, the amount of water within the synthesis of tertiary carbonic chlorinated alcohol ester and the amount of isopropanol within the synthesis of glycidylester of tertiary carbonic acid were adjusted under the circumstance, to determine the effect of the amount of water and the amount of isopropanol added to the preparation of glycidylester of tertiary carbonic acid.

Example 3

The procedure of example 1 was repeated in example 3 with the molar ratio of tertiary carbonic acid to epoxy chloropropane=1:2, the molar ratio of tertiary carbonic acid: total amount of water=1:3.24, the molar ratio of the tertiary carbonic acid to water during the synthesis of tertiary carbonic chlorinated alcohol ester=1:2.33. Specifically, the molar ratio of tertiary carbonic acid:water added: water brought by sodium hydroxide:water generated by acid base reaction=1:2.33:0.7:0.21.

The molar ratio of tertiary carbonic acid to isopropanol=1:1 within the synthesis of glycidylester of tertiary carbonic acid.

|  | Weight (g) | Volume (mL) | Moles | Molar ratio |
|---|---|---|---|---|
| (1) The preparation of tertiary carbonic chlorinated alcohol ester | | | | |
| Initial reaction materials | | | | |
| SHINA-10 acid | 226.00 | 248.35 | 1.31 | 1.00 |
| Epoxy chloropropane | 243.08 | 206.00 | 2.63 | 2.00 |
| Water | 55.00 | 55.00 | 3.06 | 2.33 |
| Sum | 524.08 | 509.35 | | |
| The addition of catalyst | | | | |
| 40% Sodium hydroxide | 27.05 | 18.92 | 0.27 | 0.21 |
| The total reaction volume | | 528.27 | | |
| (2) The synthesis of glycidylester of tertiary carbonic acid | | | | |
| Initial reaction materials | | | | |
| The products of (1) Isopropanol | 78.97 | 101.24 | 1.31 | 1.00 |
| Sum | | 101.24 | | |
| The addition of sodium hydroxide | | | | |
| First 24% sodium hydroxide | 108.97 | 86.14 | 0.65 | 0.50 |
| Second 24% sodium hydroxide | 108.97 | 86.14 | 0.65 | 0.50 |

Example 4

The procedure of example 1 was repeated in example 4 with the molar ratio of tertiary carbonic acid to epoxy chloropropane=1:2, the molar ratio of tertiary carbonic acid: the total amount of water=1:3.24, the molar ratio of the tertiary carbonic acid to water within the synthesis of tertiary carbonic chlorinated alcohol ester=1:2.33. Specifically, the molar ratio of tertiary carbonic acid:water added: water brought by sodium hydroxide:water generated by acid base reaction=1:2.33:0.7:0.21.

The molar ratio of tertiary carbonic acid to isopropanol=1:4 within the synthesis of glycidylester of tertiary carbonic acid.

|  | Weight (g) | Volume (mL) | Moles | Molar ratio |
|---|---|---|---|---|
| (1) The preparation of tertiary carbonic chlorinated alcohol ester | | | | |
| Initial reaction materials | | | | |
| SHINA-10 acid | 226.00 | 248.35 | 1.31 | 1.00 |
| Epoxy chloropropane | 243.08 | 206.00 | 2.63 | 2.00 |
| Water | 55.00 | 55.00 | 3.06 | 2.33 |
| Sum | 524.08 | 509.35 | | |
| The addition of catalyst | | | | |
| 40% Sodium hydroxide | 27.05 | 18.92 | 0.27 | 0.21 |
| The total reaction volume | | 528.27 | | |
| (2) The synthesis of glycidylester of tertiary carbonic acid | | | | |
| Initial reaction materials | | | | |
| The product of (1) Isopropanol | 315.87 | 404.97 | 5.26 | 4.00 |
| Sum | | 404.97 | | |
| The addition of sodium hydroxide | | | | |
| First 24% sodium hydroxide | 108.97 | 86.14 | 0.65 | 0.50 |
| Second 24% sodium hydroxide | 108.97 | 86.14 | 0.65 | 0.50 |

Example 5

The procedure of example 1 was repeated in example 5 with the molar ratio of tertiary carbonic acid to epoxy chloropropane=1:2, the molar ratio of tertiary carbonic acid: the total amount of water=1:10.02, the molar ratio of the tertiary carbonic acid to water within the synthesis of tertiary carbonic chlorinated alcohol ester=1:9.11. Specifically, the molar ratio of tertiary carbonic acid:water added: water brought by sodium hydroxide:water generated by acid base reaction=1:9.11:0.7:0.21.

The molar ratio of tertiary carbonic acid to isopropanol=1:1 within the synthesis of glycidylester of tertiary carbonic acid.

|  | Weight (g) | Volume (mL) | Moles | Molar ratio |
|---|---|---|---|---|
| (1) The preparation of tertiary carbonic chlorinated alcohol ester | | | | |
| Initial reaction material | | | | |
| SHINA-10 acid | 226.00 | 248.35 | 1.31 | 1.00 |
| Epoxy chloropropane | 243.08 | 206.00 | 2.63 | 2.00 |
| Water | 215.41 | 215.41 | 11.97 | 9.11 |
| Sum | 684.49 | 669.77 | | |
| The addition of catalyst | | | | |
| 40% Sodium hydroxide | 27.05 | 18.92 | 0.27 | 0.21 |
| Total reaction volume | | 688.68 | | |
| (2) The synthesis of glycidylester of tertiary carbonic acid | | | | |
| Initial reaction materials | | | | |
| The product of (1) Isopropanol | 78.73 | 100.94 | 1.31 | 1.00 |
| Sum | | 100.94 | | |
| The addition of sodium hydroxide | | | | |
| First 24% sodium hydroxide | 108.97 | 86.14 | 0.65 | 0.50 |
| Second 24% sodium hydroxide | 108.97 | 86.14 | 0.65 | 0.50 |

Example 6

The procedure of example 1 was repeated in example 6 with the volume of the reactor for preparing glycidylester of tertiary carbonic acid being 2 L and the molar ratio of tertiary carbonic acid to epoxy chloropropane=1:2, the molar ratio of tertiary carbonic acid: the total amount of water=1:10.2, the molar ratio of the tertiary carbonic acid to water within the synthesis of tertiary carbonic chlorinated alcohol ester=1:9.11. Specifically, the molar ratio of tertiary carbonic acid:water added: water brought by sodium hydroxide:water generated by acid base reaction=1:9.11:0.7:0.21.

The molar ratio of tertiary carbonic acid to isopropanol=1:4 within the synthesis of glycidylester of tertiary carbonic acid.

|  | Weight (g) | Volume (mL) | Moles | Molar ratio |
|---|---|---|---|---|
| (1) The preparation of tertiary carbonic chlorinated alcohol ester | | | | |
| Initial reaction material | | | | |
| SHINA-10 acid | 226.00 | 248.35 | 1.31 | 1.00 |
| Epoxy chloropropane | 243.08 | 206.00 | 2.63 | 2.00 |
| Water | 215.41 | 215.41 | 11.97 | 9.11 |
| Sum | 684.49 | 669.77 | | |
| The addition of catalyst | | | | |
| 40% Sodium hydroxide | 27.05 | 18.92 | 0.27 | 0.21 |
| Total reaction volume | | 688.68 | | |
| (2) The synthesis of glycidylester of tertiary carbonic acid | | | | |
| Initial reaction materials | | | | |
| The product of (1) | | | | |
| Isopropanol | 315.87 | 404.97 | 5.26 | 4.00 |
| Sum | | 404.97 | | |
| The addition of sodium hydroxide | | | | |
| First 24% sodium hydroxide | 108.97 | 86.14 | 0.65 | 0.50 |
| Second 24% sodium hydroxide | 108.97 | 86.14 | 0.65 | 0.50 |
| Initial reaction materials | | 491.11 | | |

The comparison between examples 3-6 are shown below:

|  | Example 3 | Example 4 | Example 5 | Example 6 |
|---|---|---|---|---|
| Quality Index | | | | |
| Epoxy value (EGC) | 4141 | 4100 | 4176 | 4116 |
| Purity % | 94.5 | 93.6 | 95.36 | 94 |
| Hydrogenated chloride | 489 | 524 | 366 | 509 |
| Color (Pt/Co) | 20 | 20 | 20 | 20 |
| Production Index | | | | |
| Recovering rate of epoxy chloropropane % | 96.2 | 95.8 | 95.3 | 96 |
| Recovering rate of Isopropanol | 95.1 | 94.8 | 95.8 | 96.1 |

The procedure of example 1 was repeated in the following examples 7-8 with the molar ratio of tertiary carbonic acid to epoxy chloropropane=1:20, the amount of water within the synthesis of tertiary carbonic chlorinated alcohol ester was adjusted under the circumstance.

Example 7

The procedure of example 1 was repeated in example 7 with the molar ratio of tertiary carbonic acid to epoxy chloropropane=1:20, the molar ratio of tertiary carbonic acid: the total amount of water=1:12.98, the molar ratio of the tertiary carbonic acid to water within the synthesis of tertiary carbonic chlorinated alcohol ester=1:12.07. Specifically, the molar ratio of tertiary carbonic acid:water added: water brought by sodium hydroxide:water generated by acid base reaction=1:12.07:0.7:0.21.

The molar ratio of tertiary carbonic acid to isopropanol=1:2 within the synthesis of glycidylester of tertiary carbonic acid.

|  | Weight (g) | Volume (mL) | Moles | Molar ratio |
|---|---|---|---|---|
| (1) The preparation of tertiary carbonic chlorinated alcohol ester | | | | |
| Initial reaction material | | | | |
| SHINA-10 acid | 56.50 | 62.09 | 0.33 | 1.00 |
| Epoxy chloropropane | 607.70 | 515.00 | 6.57 | 20.00 |
| Water | 71.36 | 71.36 | 3.96 | 12.07 |
| Sum | 735.56 | 648.45 | | |
| The addition of catalyst | | | | |
| 40% Sodium hydroxide | 6.76 | 4.73 | 0.07 | 0.21 |
| Total reaction volume | | 653.18 | | |
| (2) The synthesis of glycidylester of tertiary carbonic acid | | | | |
| Initial reaction materials | | | | |
| The product of (1) | | | | |
| Isopropanol | 39.66 | 50.85 | 0.66 | 2.01 |
| Sum | | 50.85 | | |
| The addition of sodium hydroxide | | | | |
| First 24% sodium hydroxide | 27.24 | 21.53 | 0.16 | 0.50 |
| Second 24% sodium hydroxide | 27.24 | 21.53 | 0.16 | 0.50 |

Example 8

The procedure of example 1 was repeated in example 8 with the molar ratio of tertiary carbonic acid to epoxy chloropropane=1:20, the molar ratio of tertiary carbonic acid: the total amount of water=1:3.76, the molar ratio of the tertiary carbonic acid to water within the synthesis of tertiary carbonic chlorinated alcohol ester=1:2.85. Specifically, the molar ratio of tertiary carbonic acid:water added: water brought by sodium hydroxide:water generated by acid base reaction=1:2.85:0.7:0.21.

The molar ratio of tertiary carbonic acid to isopropanol=1:2 within the synthesis of glycidylester of tertiary carbonic acid.

|  | Weight (g) | Volume (mL) | Moles | Molar ratio |
|---|---|---|---|---|
| (1) The preparation of tertiary carbonic chlorinated alcohol ester | | | | |
| Initial reaction material | | | | |
| SHINA-10 acid | 75.33 | 82.78 | 0.44 | 1.00 |
| Epoxy chloropropane | 810.20 | 686.61 | 8.76 | 20.00 |
| Water | 22.50 | 22.50 | 1.25 | 2.85 |
| Sum | 908.03 | 791.89 | | |
| The addition of catalyst | | | | |
| 40% Sodium hydroxide | 9.02 | 6.31 | 0.09 | 0.21 |
| Total reaction volume | | 798.20 | | |

-continued

|  | Weight (g) | Volume (mL) | Moles | Molar ratio |
|---|---|---|---|---|
| (2) The synthesis of glycidylester of tertiary carbonic acid | | | | |
| Initial reaction materials | | | | |
| The product of (1) Isopropanol | 52.88 | 67.79 | 0.88 | 2.01 |
| Sum | | 67.79 | | |
| The addition of sodium hydroxide | | | | |
| First 24% sodium hydroxide | 36.32 | 28.71 | 0.22 | 0.50 |
| Second 24% sodium hydroxide | 36.32 | 28.71 | 0.22 | 0.50 |

The comparison of the results of examples 7-8 are shown below:

|  | Example 7 | Example 8 |
|---|---|---|
| Quality Index | | |
| Epoxy value (EGC) | 4185 | 4191 |
| Purity % | 95.6 | 95.7 |
| Hydrolizable chloride | 347 | 335 |
| Color (Pt/Co) | 25 | 25 |
| Production Index | | |
| Recovering rate of epoxy chloropropane % | 96.9 | 96.5 |
| Recovering rate of isopropanol % | 95.4 | 95.9 |

The procedure of example 1 was repeated in the following examples 9-11 with the molar ratio of tertiary carbonic acid to epoxy chloropropane=1:2, the molar ratio of tertiary carbonic acid: the total amount of water=1:3.24. Specifically, the molar ratio of tertiary carbonic acid:water added: water brought by sodium hydroxide:water generated by acid base reaction=1:2.33:0.7:0.21. The solvent used within the synthesis of glycidylester of tertiary carbonic acid was changed under the circumstance.

Example 9

The solvent used within the synthesis of glycidylester of tertiary carbonic acid is anhydrous ethanol.

|  | Weight (g) | Volume (mL) | Moles | Molar ratio |
|---|---|---|---|---|
| (1) The preparation of tertiary carbonic chlorinated alcohol ester | | | | |
| Initial reaction material | | | | |
| SHINA-10 acid | 226.00 | 248.35 | 1.31 | 1.00 |
| Epoxy chloropropane | 243.08 | 206.00 | 2.63 | 2.00 |
| Water | 55.00 | 55.00 | 3.06 | 2.33 |
| Sum | 524.08 | 509.35 | | |
| The addition of catalyst | | | | |
| 40% Sodium hydroxide | 27.05 | 18.92 | 0.27 | 0.21 |
| Total reaction volume | | 528.27 | | |

-continued

|  | Weight (g) | Volume (mL) | Moles | Molar ratio |
|---|---|---|---|---|
| (2) The synthesis of glycidylester of tertiary carbonic acid | | | | |
| Initial reaction materials | | | | |
| The product of (1) Anhydrous ethanol | 157.00 | 198.99 | 3.41 | 2.60 |
| Sum | | 198.99 | | |
| The addition of sodium hydroxide | | | | |
| First 24% sodium hydroxide | 108.97 | 86.14 | 0.65 | 0.50 |
| Second 24% sodium hydroxide | 108.97 | 86.14 | 0.65 | 0.50 |

Example 10

The solvent used within the synthesis of glycidylester of tertiary carbonic acid is toluene.

|  | Weight (g) | Volume (mL) | Moles | Molar ratio |
|---|---|---|---|---|
| (1) The preparation of tertiary carbonic chlorinated alcohol ester | | | | |
| Initial reaction material | | | | |
| SHINA-10 acid | 226.00 | 248.35 | 1.31 | 1.00 |
| Epoxy chloropropane | 243.08 | 206.00 | 2.63 | 2.00 |
| Water | 55.00 | 55.00 | 3.06 | 2.33 |
| Sum | 524.08 | 509.35 | | |
| The addition of catalyst | | | | |
| 40% Sodium hydroxide | 27.05 | 18.92 | 0.27 | 0.21 |
| Total reaction volume | | 528.27 | | |
| (2) The synthesis of glycidylester of tertiary carbonic acid | | | | |
| Initial reaction materials | | | | |
| The product of (1) Toluene | 92.00 | 105.75 | 1.00 | 0.76 |
| Sum | | 105.75 | | |
| The addition of sodium hydroxide | | | | |
| First 24% sodium hydroxide | 108.97 | 86.14 | 0.65 | 0.50 |
| Second 24% sodium hydroxide | 108.97 | 86.14 | 0.65 | 0.50 |

Example 11

The solvent used within the synthesis of glycidylester of tertiary carbonic acid is ethyl acetate.

|  | Weight (g) | Volume (mL) | Moles | Molar ratio |
|---|---|---|---|---|
| (1) The preparation of tertiary carbonic chlorinated alcohol ester | | | | |
| Initial reaction material | | | | |
| SHINA-10 acid | 226.00 | 248.35 | 1.31 | 1.00 |
| Epoxy chloropropane | 243.08 | 206.00 | 2.63 | 2.00 |
| Water | 55.00 | 55.00 | 3.06 | 2.33 |
| Sum | 524.08 | 509.35 | | |

-continued

|  | Weight (g) | Volume (mL) | Moles | Molar ratio |
|---|---|---|---|---|
| The addition of catalyst |  |  |  |  |
| 40% Sodium hydroxide | 27.05 | 18.92 | 0.27 | 0.21 |
| Total reaction volume |  | 528.27 |  |  |

(2) The synthesis of glycidylester of tertiary carbonic acid

|  | Weight (g) | Volume (mL) | Moles | Molar ratio |
|---|---|---|---|---|
| Initial reaction materials |  |  |  |  |
| The product of (1) |  |  |  |  |
| Ethyl acetate | 157.80 | 177.30 | 1.79 | 1.36 |
| Sum |  | 177.30 |  |  |
| The addition of sodium hydroxide |  |  |  |  |
| First 24% sodium hydroxide | 108.97 | 86.14 | 0.65 | 0.50 |
| Second 24% sodium hydroxide | 108.97 | 86.14 | 0.65 | 0.50 |

The comparison of the results of examples 9-11 are shown below:

| Quality Index | Example 9 | Example 10 | Example 11 |
|---|---|---|---|
| Epoxy Index (EGC) | 3845 | 2912 | 2140 |
| Purity % | 87.8 | 66.4 | 48.8 |
| Color (Pt/Co) | 20 | 25 | 20 |

It can be seen from the results of the examples 9-11, when ethanol was used as solvent, the final product would have better purity and color, while toluene, ethyl acetate were used as solvents, the purity of the product obtained was not very high.

It should be noted that the examples are only the more advantageous embodiments of the present disclosure, the extent of protection of the present disclosure is not limited thereto, and the specific operation steps of the methods can be modified or replaced by technical equivalents in the present disclosure. Therefore, the modifications of the methods equivalent to the ones described in the description of the present disclosure, or direct or indirect applications of the methods in other related technical fields are all covered in the extent of protection of the present disclosure.

What is claimed is:

1. A preparation method for glycidylester of tertiary carbonic acids, comprising (1) making tertiary carbonic acid react with halo substituted epoxide with the molar ratio of tertiary carbonic acid to halo substituted epoxide being 1:1.5-20, in the presence of water and basic catalyst with the maximum amount of 30 mol% of the mole of tertiary carbonic acid with rapid stirring at 30-110° C. for 0.5 h-2.5 h; standing to stratify and then separating the lower saline water; removing and recovering unreacted halo substituted epoxide by reduced pressure distillation to obtain halo substituted alcohol ester of tertiary carbonic acid and a small amount of glycidylester of tertiary carbonic acid; (2) dissolving all products obtained from step (1) in a water-miscible aliphatic alcohol; at 20-80° C. with rapid stirring, adding alkali metal hydroxide or alkali metal alkoxide with the amount of mole equal to tertiary carbonic acid of step (1) to react; standing to stratify after reaction and separating the lower saline water; then adjusting the obtained upper organic phase to neutral by adding acidifier or by passing through $CO_2$ gas to said organic phase, and separating the salt produced; then removing the organic phase by distillation, recovering the aliphatic alcohol; then washing the obtained product with water to remove the salt remained, obtaining the glycidylester of tertiary carbonic acid product by distillation or dehydration via desiccant; wherein said water includes water added before the reaction.

2. The preparation method of claim 1, wherein for the reactants of step (1), the molar ratio of tertiary carbonic acid to the total amount of water is 1:2-14, said total amount of water including water added before the reaction, water contained in the catalyst and water produced during synthesis.

3. The preparation method of claim 2, wherein for the reactants of step (1), the molar ratio of tertiary carbonic acid to the total amount of water is 1:3.5-10.

4. The preparation method of claim 1, wherein in step (1), the basic catalyst is an alkali metal hydroxide, an alkali metal carbonate, an alkali metal hydrocarbonate or an alkali metal alkoxide.

5. The preparation method of claim 4, wherein said alkali metal hydroxide is sodium hydroxide or potassium hydroxide, said alkali metal alkoxide being alkoxide having 1-6 carbon atoms.

6. The preparation method of claim 1, wherein said acidifier is a diluted strong acid or an acidic salt.

7. The preparation method of claim 6, wherein said diluted strong acid is diluted sulphuric acid or diluted hydrochloric acid.

8. The preparation method of claim 6, wherein said acidic salt is sodium dihydrogen phosphate.

9. The preparation method of claim 1, wherein the added amount of the aliphatic alcohol in step (2) is equivalent to one to six times of the molar weight of the tertiary carbonic acid in step (1).

10. The preparation method of claim 9, wherein the added amount of the aliphatic alcohol in step (2) is equivalent to one to four times of the molar weight of the tertiary carbonic acid in step (1).

11. The preparation method of claim 9, wherein said aliphatic alcohol is isopropanol.

12. The preparation method of claim 10, wherein said aliphatic alcohol is isopropanol.

13. The preparation method of claim 1, wherein in step (1), said halo substituted epoxide is epoxy halo propane.

14. The preparation method of claim 1, wherein in step (1), said halo substituted epoxide is epoxy chloropropane, the molar ratio of said tertiary carbonic acid and said epoxy chloropropane is 1:1.8-20.

15. The preparation method of claim 5, wherein said sodium hydroxide is with the concentration of 15-40 wt %.

16. The preparation method of claim 15, wherein said sodium hydroxide is with the concentration of 20-30 wt %.

* * * * *